United States Patent [19]

Sneer

[11] 4,301,814

[45] Nov. 24, 1981

[54] CASSETTE IMPLANT

[76] Inventor: Meer Sneer, 24 Baalei Melacha St., Tel-Aviv, Israel

[21] Appl. No.: 108,170

[22] Filed: Dec. 28, 1979

Related U.S. Application Data

[63] Continuation-in-part of Ser. No. 897,535, Apr. 18, 1978, abandoned.

[51] Int. Cl.³ .............................................. A61B 10/00
[52] U.S. Cl. .................................................... 128/769
[58] Field of Search .............. 128/1 R, 213 R, 214 R, 128/749, 759, 769, 770; 3/1; 195/1.7, 1.8, 103.5, 127; 435/1-5, 29-34

[56] References Cited

U.S. PATENT DOCUMENTS

| | | | |
|---|---|---|---|
| 2,879,207 | 3/1959 | Poitras | 128/214 R |
| 3,224,434 | 12/1965 | Molonnut et al. | 128/749 |
| 3,313,289 | 4/1967 | Kapral | 3/1 |
| 3,625,198 | 12/1971 | Sparks | 128/1 R |
| 3,687,129 | 8/1972 | Nuwayser | 128/1 R |
| 3,993,560 | 11/1976 | Halpern | 128/214 R X |
| 3,998,211 | 12/1976 | Bucalo | 128/2 W X |
| 4,009,078 | 2/1977 | Wilkins et al. | 195/103.5 R |
| 4,011,861 | 3/1977 | Enger | 128/419 F |
| 4,052,754 | 10/1977 | Homsy | 128/419 F X |
| 4,087,327 | 5/1978 | Feder et al. | 195/1.7 |
| 4,104,127 | 8/1978 | Bucalo | 128/127 |

FOREIGN PATENT DOCUMENTS

| | | | |
|---|---|---|---|
| 1479002 | 7/1977 | United Kingdom | 3/1 |

OTHER PUBLICATIONS

Cooper, "A Simple Method for Growing Undifferentiated Mouse Neuroblastoma Cells," Lab Pract., vol. 24, No. 2, 2-1975.

*Primary Examiner*—John D. Yasko
*Attorney, Agent, or Firm*—Browdy and Neimark

[57] ABSTRACT

There is provided a cassette-implant for implantation in the body of mammals, comprising a housing with at least one removable and replaceable wall portion, with inlet and with outlet means for the supply of a liquid nutrient, and which cassette contains a thin disk or tablet formed member, or a plurality of stacked discs which contain one or more distinct spaces, each of which is adapted to receive a signal individual cell which is cultivated in such space, at least one of the walls being transparent; and a method for the controlled cultivation of cells by means of such cassette, while said cassette is implanted inside the body of mammals, but said cultivation being continued at will on the outside of the body while said cassette is supplied with natural or artificial nutrient media, being connected to the living body or only to a source of nutrient, said method providing means for the evaluation of the influence of various substances on the growth of a single cell, or on the growth of a number of single cells, separated from each other, and each positioned in a suitable individual receptacle for such cell, while the cassette is connected with a supply of nutrients, this being either by connection to a mammal body, or with a system of artificial circumfusion or with a system of perfusion supplying the required nutrients.

12 Claims, 8 Drawing Figures

CASSETTE IMPLANT

RELATION TO OTHER APPLICATIONS

The present patent application is a continuation-in-part of copending patent application No. 897,535 filed Apr. 18, 1978 now abandoned.

FIELD OF THE INVENTION

The invention relates to novel means for studying the behavior of an individual living cell in controlled systems of cultivation and especially while in contact with any desired inductor. More particularly, the invention relates to a novel cassette provided with inlet and outlet means, adapted to be implemented in a living body, said cassette containing a suitable support in sheet form, provided with a space or spaces adapted to accommodate a single cell, said cassette making it possible to study morphological changes of cell under the influence of various controlled factors. The novel insert can also be used for to therapeutical purposes as will be explained hereinafter. The term "controlled factors" denotes various controlled factors influencing the growth and morphology of cells, such as biological, chemical, and other factors.

The concept of the present invention is connected with that of semi-biological dental implants developed by the inventor.

The novel cassette-implant can be implanted in the body of an animal or human being, left in place for a predetermined period of time, and removed at will. When removed from the inside of the body, it can be used for continued cultivation of one or more individual cells, separated from each other, each of which is contained in a separate recessed emplacement on a suitable support, said cells being kept alive in said cassette by the supply of nutrients, it being possible to observe said cells at will so as to ascertain any change of said cells due to the influence of physical, chemical or other inductors.

STATE OF THE PRIOR ART

Various efforts have been made to obtain penetration of different cells into porous bicompatible materials so as to create a semi-biological structure comprising a firm bond between said porous structure and the tissue, i.e. between dead and living matter. Such implants are of value in the replacement of lost bone structure, in dental implants and the like.

Successes were obtained in the production of bone through transformation of loose connective tissue within hard connective tissue by the use of certain catalysts contained in bicompatible materials introduced into the test animal, such as rabbits. Similar results were obtained through penetration of loose connective tissue into porous materials sustaining the life of single cells by means of a channel connected to the rest of the organism. The results could only be observed and ascertained after killing the test animal or by biopsy, by classical histological methods. The results obtained can be interpreted only by taking into consideration the effect of the entire organism on the site of the experiment.

SUMMARY OF THE INVENTION

According to the present invention, there is provided a novel system for the in vivo and ex vivo cultivation of cells, making possible their observation at any desired stage and the influence on same of controlled factors. According to the present invention, it is possible to create semi-biological entities with different types of cells of the organism and it is possible to change the cassette containing such individual and separated cells from one organism to the other, for therapeutic purposes.

The novel device according to the present invention is in the form of a cassette of desired size and shape, having at least one detachable and replaceable wall or wall portion, at least one wall being transparent. The cassette is provided with inlet and outlet means for liquids and/or gases and can be connected to blood stream or closed circuit of natural nutrient medium, to outside sources of nutritive agents and/or to sources of chemical agents, the influence of which is examined. The cassette is filled with one or more supports: suitable supports are disks or thin tablets of any suitable material. The material may be inert and in such case it has no influence on the cultivation of the cells. It may be of a material containing an inductor which influences cell growth, and in such case the influence of the support on the growth of the cells can be observed. The support member is provided with a recessed emplacement for a single cell, which is cultivated in this specific space. The size of the recess is chosen according to the type of cell which is cultivated: it can be of the order of some tens of microns. A number of such individual recesses, each adapted to receive a single cell, which are thus separated from each other, can be provided on the same support sheet. Such recesses for individual cells can be connected with each other and with the supply system of the nutrient, by suitable channels connecting said recesses, but which are too narrow to allow movement of a cell from one space to the other. The cassette is left in place for any desired period of time during which the cell penetrates into its place, specially created, and one can observe more its development. The cells may be inspected by means of a microscope in situ, or the cassette may be removed, the removed wall or walls are replaced, and the cells may be inspected outside the growing organism. After removal of the cassette from the living organism, a single cell growth only may be continued by supplying the cell nutritive media through the inlet means provided in the cassette. The one opening can be connected to an artery, the outlet to a vein, and thus the cells in the cassette can be supplied with a constant supply of blood ensuring their further cultivation. Intercellular fluid may be passed through the cassette or there may be used an artificial nutrient medium of the type used for the cultivation of cells. One or more porous tubes may be passed through the cassette thus making possible the controlled supply of any desired gas or gaseous mixture, so as to be able to use such supply for the control or modification of cultivated cells. Ringer solution may be passed through the cassette as nutritive medium.

According to the present invention, means are provided for the observation of an individual cell growth and modification under different conditions or combinations of these, such as:

a. When implanted in the body of the animal or human;

b. outside the body but connected thereto and to the blood supply of the body;

c. removed from the vessel and supplied with nutrients from the outside.

The walls of the cassette, or at least one pair of these is made of transparent material so as to make possible the inspection of the interior of the cassette from the outside, either by visual inspection or by microscope. Openings may be provided for the removal of cell for staining or other purposes. The cassette can be made of any suitable biocompatible material, such as polymer, ceramic or metal; its size depends on the intended purpose and can vary from a few millimeters to a few centimeters. The thickness may also vary from part of a millimeter or a few millimeters. Inside the cassette there is provided a disc or discs with spaces, each for one single cell, of desired material. This will be generally a biocompatible material, but for experimental purposes a non-biocompatible material can be chosen.

BRIEF DESCRIPTION OF THE DRAWINGS

In the schematical enclosed drawings which are not according to scale.

Figure 1:
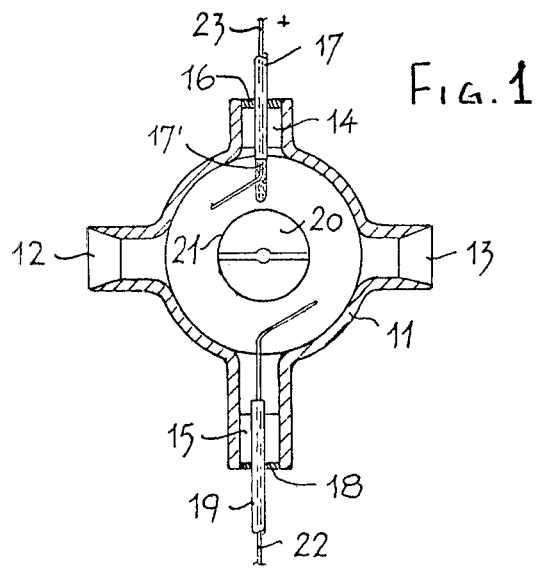
FIG. 1 is a schematical top view in section through a cassette according to the invention.

As shown in these figures, the cassette comprises a housing 11, of substantially circular outline which is provided with four openings: opening 12 which serves as entrance for the liquid nutrient medium, exit 13 of said liquid medium, entrance 14 which serves as entrance for a gaseous medium, and exit 15 for said gaseous medium. The entrance 14 and the exit 15 can be closed by means of a stopper, or there may be provided a stopper 16 with a throughgoing tube 17 which extends into the interior of housing 11, the exit 15 being provided with a stopper 18 and a tubing 19. The tubing 17 at the interior of the housing may extend into a section of porous tubing 17 while its end is closed, thus providing for the efficient introduction of small bubbles of a gaseous substance. In the interior of the housing there is provided a support member 20. This support can be a thin sheet in disk form, a thin tablet or the like. A plurality of sheets can be arranged, one on top of the other. The support may be a suitable, preferably inert plastic transparent material, provided with a small recessed emplacement for an individual cell, or with a plurality of such individual recesses adapted to receive individual single cells.

The approximate size of such recess for an individual cell is about 20 to 50 microns, such recess being connected with a supply system of nutrients by suitable channels. The support may be of any suitable material (plastic, metal, ceramic, glass or the like), and the required minute recesses and channel systems can be prepared by means of the known techniques used in the art. Such recess and channels can be etched, produced by application of pressure, cast, evaporated by a suitable beam of the type used in the production of electronic elements if a metal or ceramic is used, and the like. The housing is provided with at least one removable cover 21, which is advantageously made of transparent material.

The channels serve as supply route of nutrients and of desired chemical inductors. It is possible to observe the mitosis of a single cell, which is an important factor in cancer research and in other kinds of biological research. When a number of cells are cultivated in individual recesses, separated from each other, but interconnected by a channel system, the products of catabolism of a certain cell influences other cells in the vicinity, via said channels, and this is also an important phenomenon of investigation. Cell division can be investigated, and in such case, cultivation is commenced with a single cell and a slightly larger wall is provided for the observation of such division. This can be studied under the influence of inductors such as radiation, chemicals, gases, different nutrient media and the like.

If desired, there may be provided two electrodes 22 and 23, extending through the openings into the interior of the cassette, which electrodes are connectable to a source of a suitable current (AC or DC), providing a current while the cells are cultivated. Currents of the order of 1 microampere to about a few milliamperes are suited, which are applied at a voltage of from about 20 to 300 Volts. This provides for the possibility to study the influence of such currents on the ionic and electrolyte systems of the nutrient medium on the cells which are cultivated under the influence of such currents.

Figure 2:
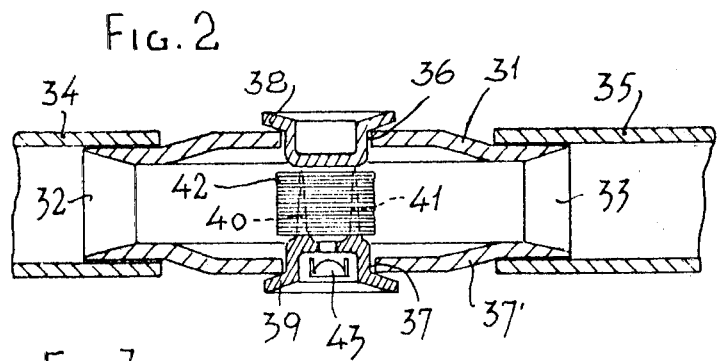
FIG. 2 is a side view, on a larger scale, of a cassette according to the invention, also in section.

A modification of the cassette illustrated in FIG. 1, is illustrated with reference to FIG. 2, in which 31 designates the housing which is made of a biocompatible material such as inert plastic, metal, ceramic or the like, and which is provided with two openings 32 and 33, which serves as inlet and outlet of a liquid nutrient supply, respectively, which is circulated through the cassette, there being provided two further openings (not shown) through which a gaseous mixture can be circulated, or through which electrodes may be inserted into the interior of the cassette. The liquid is supplied and removed via tubings 34 and 35 respectively. The upper wall of the cassette 31 is provided with an opening 36, the lower wall with an opening 37, the upper wall being provided with a tight-fitting lid 38 made of transparent material, the lower opening with a tight-fitting cover 39, both of which can be removed at will. The lower cover 39 extends into two prongs 40 and 41, which are used in order to hold in place the stack of thin disks 42 of solid sheet material, which serve as substrate on which the cell is cultivated in the cassette, which are pierced by these prongs and thus held in place. The disks 42 are thin and can be removed one at a time, while the cultivation is continued on the others. The removed disk can be examined in a conventional manner. It is also possible to observe the upper surface of the uppermost disk 42 microscopically or visually through the transparent cover 38.

At the lower part of the cassette, at its interior, there is provided a space adapted to receive a radioactive material 43, emitting a desired type of radiation, which serves to study the influence of such radiation on growing cells. Such source can be inserted and removed when desired.

A Cassette was built of about $10 \times 10 \times 3$ mm exterior dimensions wall thickness about 0.3 mm, and there was inserted in same a teflon sheet or a thin sheet of polymethylmethacrylate, provided with one or more distinct and separate recesses adapted to receive each a single cell for cultivation, with channels connecting such recesses with the source of the nutrient and/or chemical inductors, and of more than one such recess is provided, with channels interconnecting such recesses, yet maintaining the recesses as distinct entities for the cultivation of single cells. The inlet and outlet was by means of a 1 mm exterior diameter tube, and a similar porous tube passed through the cassette. The front and back walls were made of transparent methylmethacrylate, the side wall from polypropylene. The cassette was constructed in such a manner that the front wall and the rear wall can be removed and replaced; these were removed and the cassette was implanted in a test animal, left in place and removed after three months. Cell growth was inspected immediately and cell cultivation was continued for a further three months by supplying Ringer's solution. Cell modification, due to the influence of selected controlled factors, can be studied by supplying these with the nutrient medium. The cell can be inspected in the cassette from the outside by microscopial observation.

The support sheet can be made from any desired material, as set out above, and preferably a thin sheet (0.05 to 2 mm thickness), and of a suitable size (a few millimeters in diameter) is used. The individual recessed emplacements, each adapted to receive a single cell, are machined into the surface of the support member by conventional means.

The support sheet is advantageously covered with a thin transparent plastic sheet (such as cellophane or the like), or there is placed on same a thin transparent sheet similar to the support sheet. Observation of the growth and of the changes of the cell or individual cells, is generally made by inspection with an optical microscope, under regular or dark field illumination. It is possible to provide individual recessed emplacements separate from each other, the size of which is such that there is adequate space for the insertion into same of a single cell and for two cells obtained by cell division. This is important for observing cell division under the influence of various inductors.

The support sheet with the cell can be removed at will when desired, and examined in greater detail if desired by electron microscopy. The cells may be stained by conventional means and examined.

Various systems of supplying the required nutrients can be resorted to, the three basic ones being:
 a. Connection to a living organism and shunting of natural nutrient, blood or tissue fluid through the cassette, the passage being by hydrostatic pressure;
 b. Circumfusion through the cassette of an artificial nutrient medium;
 c. Perfusion through the cassette of an artificial medium;

The artificial medium can be circulated by means of a small pump.

Perfusion can be effected using hydrostatic pressure and flow regulation by conventional means.

The novel cassette provides a possibility to study an individual single cell under the influence of various nutrient media and under the influence of a variety of inductors, either each by itself or a combination of such. The observations and investigations of this kind are of importance in the study of the change of cells from normal to pathological, i.e. chemical or physical influence. It is important that single individual cells and not cell clusters be studied, as this permits a much improved observation of the change of the cell. A further important feature is the possibility to examine the individual cell or cells under cultivation while they are connected with a source of natural nutrients (either implanted in the body, such as under the skin with a suitable opening permitting observation while implanted in the body of the mammal, or on the outside of the body, but connected with a supply of nutrients from the living body), or while supplied with artificial nutrients.

When the cassette is implanted beneath the skin, such cassette can be retained in place for a few weeks, and from time to time it is possible to provide a small opening for microscopic inspection and microscopic observation.

If desired the cassette can be removed, and it can be connected outside the body with a supply of nutrients, either of synthetic nature or it can be connected with a source of blood or serum.

The novel cassette is of considerable importance and value for the evaluation of mitogenic materials and drugs. When a laboratory animal is injected with a mitogenic substance, the influence of such substance on individual and separate cells growing in the cassette can be easily examined in vivo. An experiment of this type can be carried out with a cassette containing a plurality of plastic (polyethylene) supports of 0.1 mm thickness, and such support sheets were removed from time to time for examination by classical examination techniques, while the cultivation of the individual cells and the influence of various substances was observed with the aid of further supports remaining in the cassette.

By means of the novel cassette and by means of the in vivo and/or ex vivo cultivation technique it is possible to evaluate the effect of various compounds and pharmaceutical compositions on various types of cells.

Figure 3:
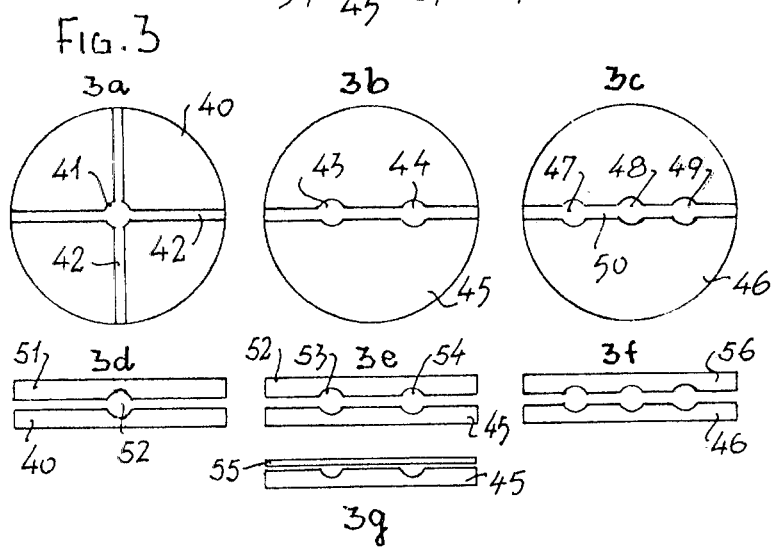
FIGS. 3a to 3c are top views, not according to scale, illustrating support members adapted to accommodate 1, 2 and 3 single cells respectively.
FIG. 3d to 3g are side views of the support members with suitable cover members.

As shown in FIG. 3a, a support sheet 40 is provided with a recessed emplacement 41, which is shown not according to scale, but in an enlarged manner. This is connected by channels 42 with the lateral edges of the support sheet 40, and these channels provide the possibility to furnish nutrients and any desired chemical inductor to a cell which is cultivated in said recess.

The support sheet shown in FIG. 3b provides space for two separate and individual cells, namely the recessed emplacements 43 and 44, shown highly enlarged, channel 45 being provided to the edge of the support sheet 45.

A further modification with three separate emplacements for single cells is shown in FIG. 3c. The support 46 is provided with emplacements 47, 48 and 49, are connected with each other and with the edge of the support sheet by channel 50.

FIG. 3d to 3g are side views of the support sheets 3a to 3c, i.e. 40, 45 and 46 respectively, with cover members shown at a small distance from the support, for illustrative purposes. In FIG. 3d there is illustrated the support sheet 40, and the corresponding cover sheet 51, which is made of transparent material and which has a corresponding recess 52.

FIG. 3e illustrates a support sheet 45, with cover member 52, which is provided with fitting recesses 53 and 54, corresponding to those of the lower support sheet, thus forming suitable spaces for the cultivation of an individual cell in each such recess.

Instead of cover member 52 there may be provided the cover member 55, which is a thin transparent plastic sheet or thin cover glass. This makes possible the closure of the space of the individual recesses and channels from above, and forms a tight fit with the support member 45 when placed on same.

FIG. 3f illustrates a support sheet 46 and a corresponding cover member 56, provided with corresponding recesses and channels.

It is clear that variations and modifications of such supports can be resorted to without departing from the scope of the invention, the principle being the use of a continuous support sheet provided with recesses adapted to accommodate a single cell and to cultivate same under the influence of various nutrients and under the influence of one or more predetermined chemical and/or physical inductors.

The above description is by way of illustration only and it is clear that various changes and modifications in the components and arrangement of same can be resorted to without departing from the scope and spirit of the invention.

I claim:

1. A Cassette implantable in a mammalian body comprising a housing with at least one transparent wall, with at least one removable and replaceable wall portion, inlet means and outlet means for a supply of nutrients and of chemicals, said housing containing a support member provided at its upper surface with one or more distinct and separate recessed emplacements, each of these adapted to receive a single cell, providing space if desired for two cells upon cell division, said recessed emplacement being connected by suitable channel means with the supply of nutrients and chemicals.

2. A Cassette according to claim 1, wherein each of the recessed emplacements is of 20 to 200 microns size.

3. A Cassette according to claim 1, wherein means are provided for supplying a gas to the interior of the cassette.

4. A Cassette according to claim 1, comprising a radioactive source.

5. A Cassette according to claim 1, wherein two opposite walls are made of transparent material.

6. A Cassette according to claim 1, wherein electrodes are provided protruding into the interior of the cassette, adapted to apply a desired voltage or electrical field to influence the cells undergoing cultivation.

7. A Cassette according to claim 1, wherein a plurality of support members are stacked on each other, transparent means being provided for covering the uppermost support member in which individual cells are cultivated in the respective recessed emplacements.

8. A process for cultivating individual cells and for investigating the influence of the various inductors on cells undergoing cultivation, which comprises cultivating such cells while located in the recessed individual emplacements of a cassette according to claim 1, supplying same either with a natural or with an artificial nutrient medium, and applying one or more chemical or physical inductor during cultivation.

9. A process according to claim 8, wherein the individual cells are cultivated while under the influence of radiation from a source of radioactive material.

10. A process according to claim 8, wherein the cassette is implanted in a mammalian body, a chemical is applied to the mammal and the influence of this chemical on cells cultivated in the cassette is evaluated.

11. A process according to claim 8, wherein the cells are cultivated while under the influence of an electric voltage.

12. A process according to claim 8, wherein cell cultivation is effected under the influence of a single inductor or under the influence of any combination of more than one inductor.

* * * * *

UNITED STATES PATENT AND TRADEMARK OFFICE
CERTIFICATE OF CORRECTION

PATENT NO. : 4,301,814
DATED : November 24, 1981
INVENTOR(S) : Meer SNEER

It is certified that error appears in the above–identified patent and that said Letters Patent are hereby corrected as shown below:

On The Title Page Insert:

-- [30] Foreign Application Priority Data
April 26, 1977 Israel . . . . . . S.N. 51942 --

Signed and Sealed this

Twenty-third Day of November 1982

[SEAL]

Attest:

Attesting Officer

GERALD J. MOSSINGHOFF

Commissioner of Patents and Trademarks